United States Patent
Bracht

(10) Patent No.: US 7,029,692 B1
(45) Date of Patent: Apr. 18, 2006

(54) TRANSDERMAL THERAPEUTIC SYSTEM WITH NICOTINE AND ADDITION OF MONOTERPENE KETONES

(75) Inventor: Stefan Bracht, Ochtendung (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 299 days.

(21) Appl. No.: 09/937,534

(22) PCT Filed: Mar. 21, 2000

(86) PCT No.: PCT/EP00/02457

§ 371 (c)(1), (2), (4) Date: Sep. 26, 2001

(87) PCT Pub. No.: WO00/57824

PCT Pub. Date: Oct. 5, 2000

(30) Foreign Application Priority Data

Mar. 26, 1999 (DE) ................... 199 13 732

(51) Int. Cl.
A61L 15/44 (2006.01)
A61F 13/02 (2006.01)

(52) U.S. Cl. .............. 424/449; 424/439; 424/449

(58) Field of Classification Search ............... 424/448, 424/449, 443, 439
See application file for complete search history.

(56) References Cited

U.S. PATENT DOCUMENTS

| 3,559,655 | A | * | 2/1971 | Brisken et al. | ............... 131/2 |
| 4,039,653 | A | * | 8/1977 | DeFoney et al. | ............. 424/19 |
| 4,933,184 | A | | 6/1990 | Tsuk | |
| 5,128,135 | A | | 7/1992 | Morimoto et al. | |
| 5,362,496 | A | | 11/1994 | Baker et al. | |
| 5,363,496 | A | * | 11/1994 | Baker et al. | ............. 424/435 |
| 5,593,684 | A | | 1/1997 | Baker et al. | |
| 5,599,554 | A | * | 2/1997 | Majeti | ............. 424/448 |
| 5,820,877 | A | * | 10/1998 | Yamaguchi et al. | ........ 424/449 |

FOREIGN PATENT DOCUMENTS

| EP | 0356382 | 2/1990 |
| WO | 95/01788 | 1/1995 |
| WO | WO 9508324 | 3/1995 |

* cited by examiner

Primary Examiner—Thurman K. Page
Assistant Examiner—Micah-Paul Young
(74) Attorney, Agent, or Firm—Jordan and Hamburg LLP

(57) ABSTRACT

A transdermal therapeutic system having a backing layer, at least one nicotine-containing layer ore zone, which may have pressure-sensitive properties, as well as a removable protective layer is characterized by a content of at least one essential oil extracted from a mint species, or at least one monoterpene ketone contained in these essential oils.

8 Claims, 1 Drawing Sheet

TRANSDERMAL THERAPEUTIC SYSTEM WITH NICOTINE AND ADDITION OF MONOTERPENE KETONES

Figure 1:
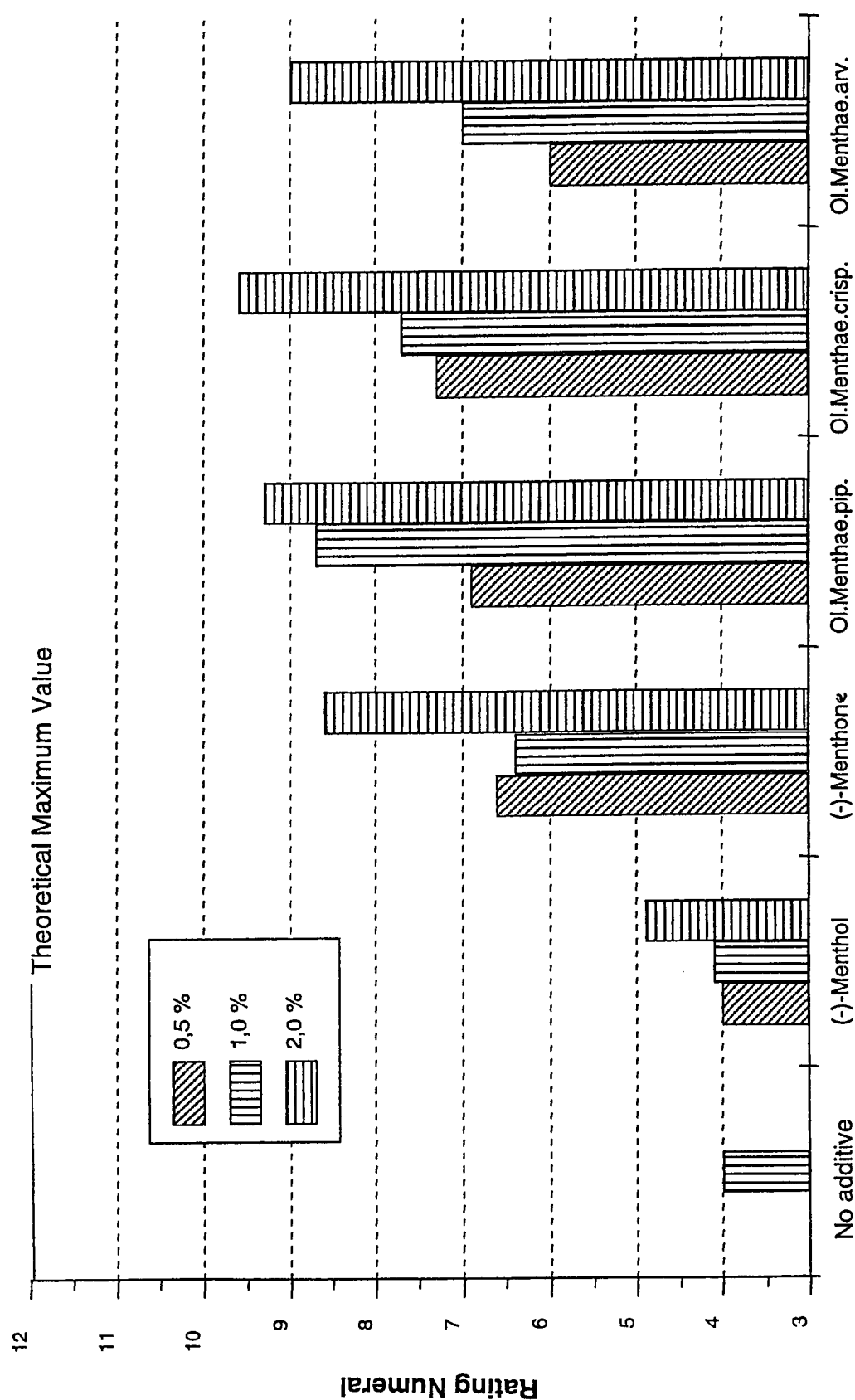

The present invention relates to the addition of odour-improving substances to transdermal therapeutic systems (TTSs) containing nicotine. More particularly it relates to nicotine-comprising TTSs containing such additives, as well as to processes for masking the unpleasant smell of such TTSs, as well as to the use of odour-improving substances for masking the unpleasant smell of such TTSs caused by the nicotine content.

Worldwide, nicotine-containing TTSs are widely used in smoking cessation treatment. However, the systems available on the market exhibit a distinct nicotine smell, which is perceived especially when removing the systems from the package and upon application thereof.

In the course of the storage period of typically 2 to 3 years, owing to partial degradation, a marked intensification of this smell and a change up to subjectively very unpleasant types of smells can occur.

WO 95/08324 A1 describes a process for making TTSs of at least two layers, using a highly volatile ingredient as exclusive solvent. These TTSs may contain various active agents, including nicotine as well as, inter alia, menthol or other volatile terpene derivatives, as skin penetration enhancer. No special action of these additives with respect to smell in nicotine-comprising TTSs has been described. As regards the "volatile terpene derivatives" no differentiation is made between monoterpene alcohols and monoterpene ketones.

EP 0 356 382 A2 discloses TTSs based on certain block copolymers, wherein also nicotine may be used as an active agent. To improve skin penetration, eucalyptol or eucalyptus oils are proposed, putting special emphasis on cineol as main component; ingredients of mint oils are not considered. The aspect of the unpleasant smell of nicotine-comprising patches has likewise not been considered.

U.S. Pat. No. 5,599,554 A concerns the transmucosal or transdermal application of nicotine, wherein the compositions employed may also contain odoriferous substances or flavours. The characteristic smell of nicotine is mentioned, it us true, but it is not described as being of disadvantage. Aromatic compounds such as menthol or eucalyptol, but not essential mint oils or terpene ketones, are mentioned as optional ingredients. No indication is made of the function of those additives. Presumably, they serve to improve taste in oral administration forms.

U.S. Pat. No. 5,593,684 A describes a method for treatment based on the simultaneous transmucosal and transdermal administration of nicotine. Here, terpene-containing plant secretions are employed as "etherial oils" in lozenges for oral application in order to mask the unpleasant taste of nicotine.

U.S. Pat. No. 4,933,184 concerns TTSs with improved transdermal active substance delivery, inter alia for nicotine, with menthol being utilized as enhancer; no mention is made of other substances occurring in etherial oils of mint species, e.g. monoterpene ketone. A mint oil was examined as enhancer, as an alternative to menthol, but surprisingly did not yield that effect. As for the rest, this publication merely relates to the improvement of active substance permeation, not to a process for improving the smell of TTSs.

It is thus the object of the present invention in nicotine-containing TTSs according to the introductory part of claim 1, to neutralise this characteristic smell, or mask it with a more pleasant smell, by adding suitable odoriferous substances.

The solution of this task has now been found in the addition of essential oils of various mint species or of components thereof, especially of monoterpene ketones. In accordance with the invention, these additives can be used to mask or improve the unpleasant smell of nicotine-comprising TTSs. The TTSs according to the invention have a content of at least one essential oil extracted from a mint species, or of a monoterpene ketone occurring in these essential oils.

The components of the essential oils of various mint species are dominated by products of the terpene metabolism, more precisely by monoterpenes.

Mint oils are generally characterized by their pleasant, refreshing smell. Examples of oils used are peppermint oil, spearmint oil or poleimin oil, each extracted from different plants.

The characteristic monoterpenes contained in these oils can be subdivided into monoterpene alcohols and monoterpene ketones.

Typical monoterpene alcohols are: menthol, isomenthol, neomenthol, neoisomenthol and isopulegol. Typical monoterpene ketones are: menthone, isomenthone, carvone, piperitone, pulegone and isopulegone. Practically all of these representatives exist as enantiomers both in an optically levorotatory and a dextrorotatory form.

As representatives of this group the essential oils of peppermint (Oleum Menthae peperitae), spearmint (Oleum Menthae crispae) and (Japanese) mint (Oleum Menthae arvensis) were examined.

Peppermint oil and especially mint oil are dominated by monoterpene alcohols, especially menthol. Spearmint oil, by contrast, contains above all monoterpene ketones, especially carvone (cf. monograph "Pfefferminzöl" [Peppermint oil] in the European Pharmacopeia 1997; monograph "Minzöl" [Mint Oil] in the German Pharmacopeia 1997; as well as G. Schneider: Pharmazeutische Biologie [Pharmaceutic Biology], 2nd ed. 1988, BI Wissenschaftsverlag, S. 342–345).

As single substances, (−)-menthol and (−)-menthone were tested as typical monoterpene alcohol and typical monoterpene ketone, respectively.

EXAMPLES

To examine the effect of such additives, a simplified smelling-test model was devised.

Nicotine was mixed in a concentration of 7%-wt. with miglyol 812. Miglyol 812 is a saturated triglyceride serving as an odourless carrier. The concentration of 7%-wt. of nicotine corresponds approximately to the active substance concentration used in TTSs of 5–10%-wt. For nicotine in miglyol, a vapour pressure comparable to that of TTSs, and thus a similar intensity of smell, results. To this test mixture were added 5 test substances or test mixtures:

(−)-Menthol, (−)-menthone, peppermint oil (quality according to European Pharmacopeia), spearmint oil (quality according to Deutscher Arzneimittel Codex DAC [German Codex of Pharmaceutics] and mint oil (quality according to German Pharmacopeia).

The quantities added amounted to 0.5, 1.0 and 2.0%-wt. in each case.

This yielded 15 test samples. In addition, one sample was prepared without odour-improving additive.

These 16 sample were assessed by 6 subjects as to odour, with the kind and amount of the respective additive not being known to the subjects.

The assessment criteria and rating numerals comprise:

| 1. Nicotine smell: | imperceptible (4); faint (3); moderate (2); distinct (1) |
|---|---|
| 2. Overall impression: | unpleasant (1); neutral (2); pleasant (3); fragrant (4) |

The assessment of the overall impression was multiplied by the factor 2, for greater emphasis as against the nicotine smell, before adding the two values for each sample and person. Higher values signify a more favourable assessment. The rating numerals were used to form the mean value. The theoretical minimal value is 3.0 and the theoretical maximum value is 12.0.

The results are shown in Table 1:

| Test produkt/Amount | 0.5%-wt. | 1.0%-wt. | 2.0%-wt. |
|---|---|---|---|
| (−)-Menthol | 4.0 | 4.1 | 4.9 |
| (−)-Menthone | 6.6 | 6.4 | 8.6 |
| Peppermint oil | 6.9 | 8.7 | 9.3 |
| Spearmint oil | 7.3 | 7.7 | 9.6 |
| Mint oil | 6.0 | 7.0 | 9.0 |

The product without additive yielded the value 4.0.

A graphic representation of the results is shown in FIG. 1.

This shows a very surprisingly clear advantage of menthone over menthol. The 1 ss favourable results of mint oil, which is dominated by menthol (G. Schneider; Pharmazeutische Biologie, 2nd ed. 1988, BI Wissenschaftsverlag, p. 345) as compared to peppermint oil, typically containing up to 32% of menthone (European Pharmacopeia 1997), is supportive of these findings.

Finally, spearmint oil, which is dominated by carvone and is practically free from menthol, yielded the best results.

Overall, this demonstrates a clear advantage of monoterpene ketones, or mixtures of monoterpene alcohols and monoterpene ketones, over pure monoterpene alcohols.

The practical realisation of adding the substances according to the invention to nicotine-containing TTSs meets with certain difficulties because of the high volatility of the substances; however, these difficulties can be eliminated by observing the teaching of PCT/WO 95/08324.

The quantity of monoterpene ketone(s) or of essential oil contained in the nicotine-comprising matrix of the odour-improved TTSs according to the invention amounts to 0.1 to 5.0%-wt., preferably 0.5 to 2%-wt.

Thus, the addition of substances according to the present invention to nicotine-containing TTSs constitutes a useful means for improving the unpleasant smell of such TTSs.

The TTSs possessing the features as described in the introductory part of claim 1 are characterized, as mentioned above, by a content of at least one essential oil extracted from a mint species, or a monoterpene ketone occurring in these essential oils.

Preferably the monoterpene ketone is one from the group of carvone, dihydrocarvone, menthone, isopulegone, isomenthone, neomenthone, neoisomenthone or piperitone. The monoterpene ketones may be utilized as pure enantiomers or mixtures thereof.

As essential oil, peppermint oil (Oleum Menthae crispae) is used with particular preference.

The content of monoterpene ketone(s) or of essential oils in the nicotine-containing matrix is preferably 0.1 to 5.0%-wt., especially preferred 0.5 to 2%-wt.

The invention further relates to a process for masking an unpleasant smell, caused by a content of nicotine, of a transdermal therapeutic system, this process being characterized in that at least one odour-improving substance is added to the nicotine-containing transdermal therapeutic system, said substance being an essential oil extracted from a mint species, or being a monoterpene ketone contained in an essential oil extracted from a mint species.

Here, preferably, the monoterpene ketones mentioned above or peppermint oil may be used as monoterpene ketones or essential oil, respectively, it being possible to utilize the monoterpene ketones as pure enantiomers or as mixtures thereof.

The monoterpene ketone(s) or the essential oil(s) of the nicotine-containing matrix are preferably used in a concentration of 0.1 to 5.0%-wt, especially preferred in a concentration of 0.5 to 2%-wt.

Further, the invention comprises the use of an essential oil extracted from a mint species and/or of a monoterpene ketone contained in an essential oil extracted from a mint species, for masking an unpleasant smell of a transdermal therapeutic system, said smell being caused by a content of nicotine in said transdermal therapeutic system.

Preferably, the monoterpene ketone used is one from the group of carvone, dihydrocarvone, menthone, isopulegone, isomenthone, neomenthone, neoisomenthone or piperitone, it being possible to use the monoterpene ketones as pure enantiomers or as mixtures thereof.

As essential oil, peppermint oil (Oleum Menthae crispae) is used with particular preference.

In the use according to the invention for masking an unpleasant smell of a nicotine-containing transdermal therapeutic system, the monoterpene ketone(s) or the essential oil are/is added to the nicotine-containing matrix preferably in a concentration of 0.1 to 5.0%-wt, particularly preferred in a concentration of 0.5 to 2%-wt.

What is claimed is:

1. Transdermal therapeutic system comprising a backing layer, at least one nicotine-containing layer or zone, and an additive comprising at least one monoterpene ketone, wherein the content of at least one monoterpene ketone in the nicotine-containing layer or zone is 0.1 to 5.0%-wt of the weight of the layer or zone.

2. Transdermal therapeutic system according to claim 1, wherein the monoterpene ketone is selected from the group consisting of carvone, dihydrocarvone, menthone, isopulegone, isomenthone, neomenthone, neoisomenthone and piperitone.

3. Transdermal therapeutic system according to claim 2, wherein the monoterpene ketone is a pure enantiomer thereof or a mixture of enantiomers thereof.

4. Process for masking an unpleasant smell, caused by the presence of nicotine, comprising adding to a nicotine-containing layer or zone of a nicotine-containing transdermal therapeutic system, 0.1 to 5.0%-wt, based on the weight of the layer or zone, of at least one monoterpene ketone.

5. Process according to claim 4, wherein the monoterpene ketone is selected from the group consisting of carvone, dihydrocarvone, menthone, isopulegone, isomenthone, neomenthone, neoisomenthone and piperitone.

6. Transdermal therapeutic system according to claim 1, wherein the nicotine-containing layer or zone has pressure-sensitive adhesive properties and is covered by a removable protective layer.

7. Transdermal therapeutic system according to claim 1, wherein the content of the at least one monoterpene ketone in the nicotine-containing layer or zone is 0.5–2%-wt of the weight of the layer or zone.

8. Process according to claim 4, wherein the at least one monoterpene ketone is added to the nicotine-containing layer or zone in a quantity constituting 0.5–2% wt of said layer or zone.

* * * * *